US009339658B2

(12) United States Patent
Dong et al.

(10) Patent No.: US 9,339,658 B2
(45) Date of Patent: *May 17, 2016

(54) ADAPTIVE EVENT STORAGE IN IMPLANTABLE DEVICE

(71) Applicant: Cardiac Pacemakers, Inc., St. Paul, MN (US)

(72) Inventors: Yanting Dong, Lexington, KY (US); David L. Perschbacher, Coon Rapids, MN (US); Jeffrey E. Stahmann, Ramsey, MN (US); Dan Li, Shoreview, MN (US); Deepa Mahajan, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/173,111

(22) Filed: Feb. 5, 2014

(65) Prior Publication Data
US 2014/0155958 A1    Jun. 5, 2014

Related U.S. Application Data

(63) Continuation of application No. 12/781,459, filed on May 17, 2010, now Pat. No. 8,649,860.

(60) Provisional application No. 61/181,542, filed on May 27, 2009.

(51) Int. Cl.
*A61N 1/39* (2006.01)
*A61N 1/02* (2006.01)
(Continued)

(52) U.S. Cl.
CPC ............ *A61N 1/37252* (2013.01); *A61N 1/025* (2013.01); *A61N 1/3621* (2013.01); *A61N 1/3702* (2013.01); *A61N 1/372* (2013.01)

(58) Field of Classification Search
USPC .......................................... 607/17
See application file for complete search history.

(56) References Cited

U.S. PATENT DOCUMENTS 4,223,678 A    9/1980 Langer et al.
4,374,382 A    2/1983 Markowitz
(Continued)

FOREIGN PATENT DOCUMENTS

JP    2004261580 A    9/2004
JP    2006110180 A    4/2006
(Continued)

OTHER PUBLICATIONS

"U.S. Appl. No. 12/781,459, Response filed Jul. 31, 2013 to Non Final Office Action mailed May 17, 2013", 12 pgs.
(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

Monitoring physiological parameter using an implantable physiological monitor in order to detect a condition predictive of a possible future pathological episode and collecting additional physiological data associated with the condition predictive of a possible future pathological episode. Monitoring another physiological parameter in order to detect a condition indicative of the beginning of a present pathological episode and collecting additional pathological data in response to the condition. Determining that the condition predictive of a future episode and the condition indicative of a present episode are associated and, in response thereto, storing all the collected physiological data.

19 Claims, 13 Drawing Sheets

(51) Int. Cl.
  *A61N 1/372* (2006.01)
  *A61N 1/362* (2006.01)
  *A61N 1/37* (2006.01)

(56) References Cited

U.S. PATENT DOCUMENTS

| | | | |
|---|---|---|---|
| 4,556,063 A | | 12/1985 | Thompson et al. |
| 4,583,553 A | | 4/1986 | Shah et al. |
| 5,007,431 A | | 4/1991 | Donehoo, III |
| 5,312,446 A | | 5/1994 | Holschbach et al. |
| 5,518,001 A | | 5/1996 | Snell |
| 5,522,850 A | * | 6/1996 | Yomtov et al. ............... 607/5 |
| 5,730,143 A | | 3/1998 | Schwarzberg |
| 5,817,134 A | | 10/1998 | Greenhut et al. |
| 5,908,392 A | | 6/1999 | Wilson et al. |
| 5,944,745 A | | 8/1999 | Rueter |
| 6,200,265 B1 | | 3/2001 | Walsh et al. |
| 6,285,909 B1 | | 9/2001 | Sweeney et al. |
| 6,301,503 B1 | | 10/2001 | Hsu et al. |
| 6,360,122 B1 | | 3/2002 | Fischell et al. |
| 6,526,314 B1 | | 2/2003 | Eberle et al. |
| 6,589,187 B1 | | 7/2003 | Dirnberger et al. |
| 6,599,242 B1 | | 7/2003 | Splett et al. |
| 6,788,970 B1 | | 9/2004 | Park et al. |
| 6,823,210 B2 | | 11/2004 | Eberle et al. |
| 6,843,801 B2 | | 1/2005 | Conley et al. |
| 6,907,289 B2 | | 6/2005 | Stahmann et al. |
| 7,418,295 B2 | | 8/2008 | Conley et al. |
| 7,421,292 B1 | | 9/2008 | Kroll |
| 7,447,544 B1 | | 11/2008 | Kroll |
| 8,649,860 B2 | * | 2/2014 | Dong et al. ............... 607/5 |
| 2004/0138536 A1 | | 7/2004 | Frei et al. |
| 2004/0215270 A1 | | 10/2004 | Ritscher et al. |
| 2004/0230105 A1 | | 11/2004 | Geva et al. |
| 2005/0081847 A1 | | 4/2005 | Lee et al. |
| 2005/0171448 A1 | | 8/2005 | Korzinov et al. |
| 2005/0203366 A1 | | 9/2005 | Donoghue et al. |
| 2006/0058850 A1 | | 3/2006 | Kramer et al. |
| 2007/0255147 A1 | | 11/2007 | Drew et al. |
| 2008/0058651 A1 | | 3/2008 | Shen et al. |
| 2010/0305642 A1 | | 12/2010 | Dong et al. |

FOREIGN PATENT DOCUMENTS

| | | |
|---|---|---|
| WO | WO-9736647 A1 | 10/1997 |
| WO | WO-2010138332 A1 | 12/2010 |
| WO | WO-2010138332 A8 | 12/2010 |

OTHER PUBLICATIONS

"U.S. Appl. No. 12/781,459, Corrected Notice of Allowance mailed Jan. 14, 2014".

"U.S. Appl. No. 12/781,459, Examiner Interview Summary mailed Apr. 8, 2013", 3 pgs.

"U.S. Appl. No. 12/781,459, Examiner Interview Summary mailed Sep. 24, 2012", 3 pgs.

"U.S. Appl. No. 12/781,459, Non Final Office Action mailed Jan. 3, 2013", 8 pgs.

"U.S. Appl. No. 12/781,459, Non Final Office Action mailed May 17, 2013", 8 pgs.

"U.S. Appl. No. 12/781,459, Non Final Office Action mailed Aug. 21, 2012", 8 pgs.

"Application U.S. Appl. No. 12/781,459, Notice of Allowance mailed Sep. 27, 2013", 9 pgs.

"U.S. Appl. No. 12/781,459, Response filed Apr. 3, 2013 to Non Final Office Action mailed Jan. 3, 2013", 11 pgs.

"U.S. Appl. No. 12/781,459, Response filed Nov. 20, 2012 to Non Final Office Action mailed Aug. 21, 2012", 12 pgs.

"European Application Serial No. 10719982.0, Examination Notification Art. 94(3) mailed Nov. 8, 2013", 4 pgs.

"International Application Serial No. PCT/US2010/035133, Int. Prelim Report on Patentability mailed Dec. 8, 2011", 8 pgs.

"International Application Serial No. PCT/US2010/035133, International Search Report mailed Jul. 20, 2010", 5 pgs.

"International Application Serial No. PCT/US2010/035133, Written Opinion mailed Jul. 20, 2010", 7 pgs.

"Japanese Application Serial No. 2012-513101, Office Action mailed Jul. 9, 2013", 3 pgs.

"Japanese Application Serial No. 2012-513101, Response filed Oct. 7, 2013 to Office Action mailed Jul. 9, 2013", 5 pgs.

\* cited by examiner

ADAPTIVE EVENT STORAGE IN IMPLANTABLE DEVICE

CROSS-REFERENCE TO RELATED APPLICATIONS

This application is a continuation of U.S. application Ser. No. 12/781,459, now U.S. Pat. No. 8,649,860 filed May 17, 2010, which claims the benefit of U.S. Provisional Application No. 61/181,542, filed on May 27, 2009, under 35 U.S.C. §119(e), which is hereby incorporated by reference in its entirety.

BACKGROUND

Cardiac rhythm management devices can include implantable devices that provide electrical stimulation to selected chambers of the heart in order to treat disorders of cardiac rhythm. For example, an implantable pacemaker can deliver timed pacing pulses to the heart to treat bradyarrhythmia, in which the heart rate can be too slow. In another example of a cardiac rhythm management device, an implantable cardioversion/defibrillator can deliver antitachyarrhythmia pacing (ATP) or a cardioversion or defibrillation shock to treat tachyarrhythmia, in which the heart rate can be too fast, and can also include bradyarrhythmia pacing capability. In yet another example, implantable cardiac resynchronization therapy (CRT) devices can deliver pacing-level pulses to spatially coordinate the heart contraction (with or without altering heart rate) for obtaining a more efficient contraction to improve cardiac output, and such capability can be combined with pacers, cardioverters, or defibrillators. In an even further example, implantable neurostimulation devices can be used to deliver electrical energy to a desired portion of the autonomic nervous system, such as to stimulate or inhibit one of the sympathetic or parasympathetic nervous systems to adjust an autonomic balance to impact cardiovascular performance.

Overview

Cardiac rhythm management devices can be programmed with a number of different parameter settings that affect the manner in which therapy is delivered. These parameters can be initially programmed after implantation while a physician is monitoring the patient. In such a case, the physician may program the device based on electrogram or other physiological information available in the acute clinical setting. The patient's condition can later change, however. Capturing accurate electrogram or other physiological information obtained over a longer period of time, such as chronically between regularly-scheduled outpatient office visits, can help the physician re-program the device, if needed, or to diagnose and assess the patient's condition.

The present inventors have recognized, among other things, that traditional approaches to recording tachyarrhythmia or other episode data, can fail to record the true onset of the condition. Missing the episode's onset can render the recorded data useless to a treating physician. Onset information can be missed due to memory constraints present in a cardiac rhythm management device. The present systems and methods can address capturing the true onset of a tachyarrhythmia episode or the like, such as through the use of multiple data buffers and additional trigger criteria, among other things.

In Example 1, a system includes an implantable physiological data monitor, a processor, a static memory buffer, a rolling memory buffer, and a memory. The implantable physiological data monitor is configured to monitor one or more physiological data parameters. The processor is coupled to the implantable physiological data monitor and configured to detect conditions predictive of a possible future pathological episode and indicative of the beginning of a present pathological episode. Detection of the condition predictive of a possible future pathological episode is accomplished using a first physiological data parameter monitored by the implantable physiological data monitor. Detection of the condition indicative of the beginning of a present pathological episode is accomplished using a second physiological data parameter monitored by the implantable physiological data monitor. The static memory buffer is configured to store a time segment of a third physiological data parameter when triggered by the detection of the condition predictive of a possible future pathological episode. The rolling memory buffer is configured to store a fixed segment of a fourth physiological data parameter. Both the third and fourth physiological data parameters are monitored by the implantable physiological data monitor. The memory is configured to store the data retained in the static memory buffer and the rolling memory buffer. Storage to the memory is triggered by detection of the condition indicative of the beginning of a present pathological episode.

In Example 2, the processor of Example 1 is also configured to determine that the condition predictive of a future pathological episode is associated with the present pathological episode. In response to making the determination, the data retained in the static memory buffer will be associated with the data retained in the rolling memory buffer.

In Example 3, the processor of Example 2 is configured to determine that the two conditions are associated at least in part by determining that the condition predictive of a future episode occurred within a specified time of the present pathological episode.

In Example 4, the system of Example 2 determines that the condition predictive of a future pathological episode is associated with the present pathological episode by determining that the predictive condition substantially persisted until the present pathological episode began. The determination can also include a specified time period over which the predictive condition persisted.

In Example 5, the system of Example 4 determines that the predictive condition substantially persisted between the initial detection and the detection of the condition indicative of the beginning of a present pathological episode condition, except for a period of time.

In Example 6, the pathological episode of any one or more of Examples 1-5 optionally include an arrhythmic episode.

In Example 7, the detection of either of the conditions in any one or more of the Examples 1-6 includes detecting when at least a specified number of consecutive measurements of the physiological data parameter meets a test.

In Example 8, the detection of either of the conditions in any one or more of Examples 1-6 includes detecting when a rate of change of the physiological data meets a test and there is no indication of physical exertion detected.

In Example 9, at least two of the first, second, third, and fourth physiological data parameters of any one or more of Examples 1-8 represent the same physiological characteristic.

In Example 10, at least two of the first, second third, and fourth physiological data parameters of any one or more of Examples 1-8 represent a different physiological characteristic.

In Example 11, at least the first and second physiological data parameters of any one or more of Examples 1-8 represent the same physiological characteristic. Additionally, in Example 11, the monitored physiological characteristic includes at least on of heart rate, electrogram morphology, blood pressure, blood gas, blood chemistry, respiration rate, atrial versus ventricular heart rate, heart rate onset, or heart rate stability.

In Example 12, the monitoring module of any one of Examples 1-11 is configured to monitor one or more of an electrocardiogram sensor, a heart rate sensor, a heart sounds sensor, a pressure sensor, a blood gas sensor, an electroneurogram sensor, a posture sensor, a respiratory sensor, or a chemical sensor.

In Example 13, a method includes monitoring a first physiological data parameter, detecting a condition predictive of a possible future pathological episode, collecting a second physiological data parameter, monitoring a third physiological data parameter, detecting a condition indicative of a beginning of a present pathological episode, and collecting a fourth physiological data parameter. Monitoring the first and third physiological data parameters is done using an implantable physiological data parameter. Collecting the second physiological data parameter is done in response to detecting the condition predictive of a possible future pathological episode. The second physiological data parameter is associated with the condition predictive of a possible future pathological episode. Collecting the fourth physiological data parameter is done response to detecting the condition indicative of the beginning of a present pathological episode. The fourth physiological data parameter is associated with the condition indicative of the beginning of a present pathological episode.

In Example 14, the method of Example 1 also includes determining that the condition predictive of a possible future pathological episode is associated with the present pathological episode. Additionally, in response to determining the condition is associated to the present pathological episode, the method of Example 1 also stores the collected second physiological data in association with the fourth physiological data.

In Example 15, the determining that the predictive condition is associated with the present pathological episode of Example 14 optionally includes determining that the predictive condition occurred within a specified time period of the present pathological episode.

In Example 16, the determining that the predictive condition is associated with the present pathological episode of Example 14 optionally includes determining that the predictive condition substantially persisted for a specified time period until the condition indicative of the beginning of a present pathological episode was detected.

In Example 17, the determining that the predictive condition substantially persisted of Example 16 includes detecting a period of time, between the initial detection of the predictive condition and the detection of the condition indicative of the beginning of a present pathological episode, during which the predictive condition was not present.

In Example 18, detecting the predictive condition of any one or more of Examples 13-17 includes detecting a condition predictive of a possible future arrhythmic episode.

In Example 19, detecting one of the conditions of any one or more of Examples 13-18 includes detecting that at least a specified number of consecutive measurements of the monitored physiological data parameter meet a test.

In Example 20, detecting one of the conditions of any one or more of Examples 13-18 includes detecting a rate of change of the monitored physiological data parameter meets a test and no corresponding indication of physical exertion is detect.

In Example 21, at least two of the first, second, third, and fourth physiological data parameters of any one or more of Examples 13-20 represent the same physiological characteristic.

In Example 22, at least two of the first, second third, and fourth physiological data parameters of any one or more of Examples 13-20 represent a different physiological characteristic.

In Example 23, at least the first and second physiological data parameters of any one or more of Examples 13-20 represent the same physiological characteristic. Additionally, in Example 23, the monitored physiological characteristic includes at least on of heart rate, electrogram morphology, blood pressure, blood gas, blood chemistry, respiration rate, atrial versus ventricular heart rate, heart rate onset, or heart rate stability.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As described above, when attempting to re-program a CRM device, physicians can benefit from detailed information regarding device performance, especially information about pathological episodes, such as an arrhythmia or the like. The following describes methods and systems for providing physicians with detailed information, such as electrogram (EGM) data, including capturing onset data for a tachyarrhythmia or other pathological episode.

Figure 1A:
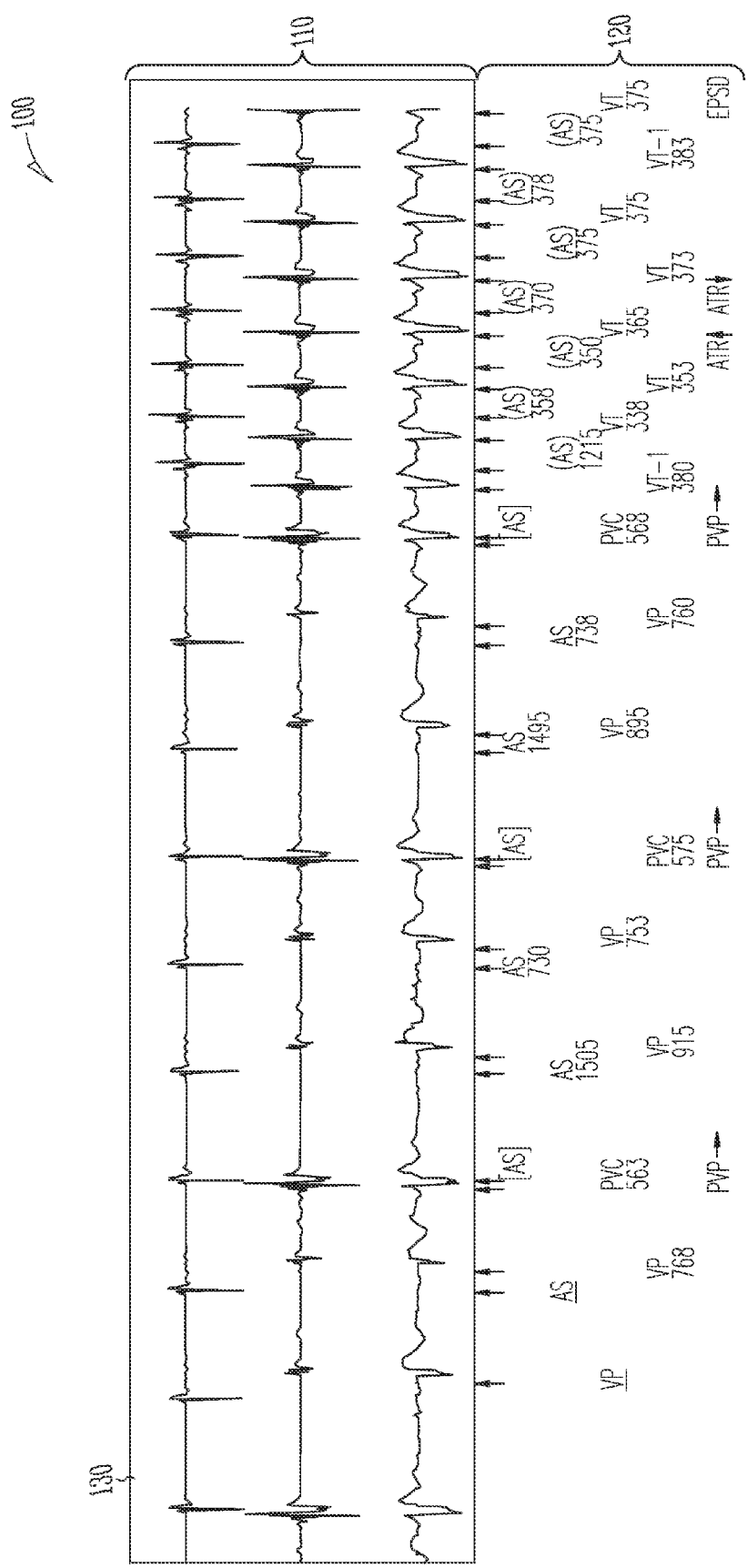
FIGS. 1A-1B are example reproductions of multiple timeline segments of electrogram data illustrating an arrhythmia episode.
Figure 1B:
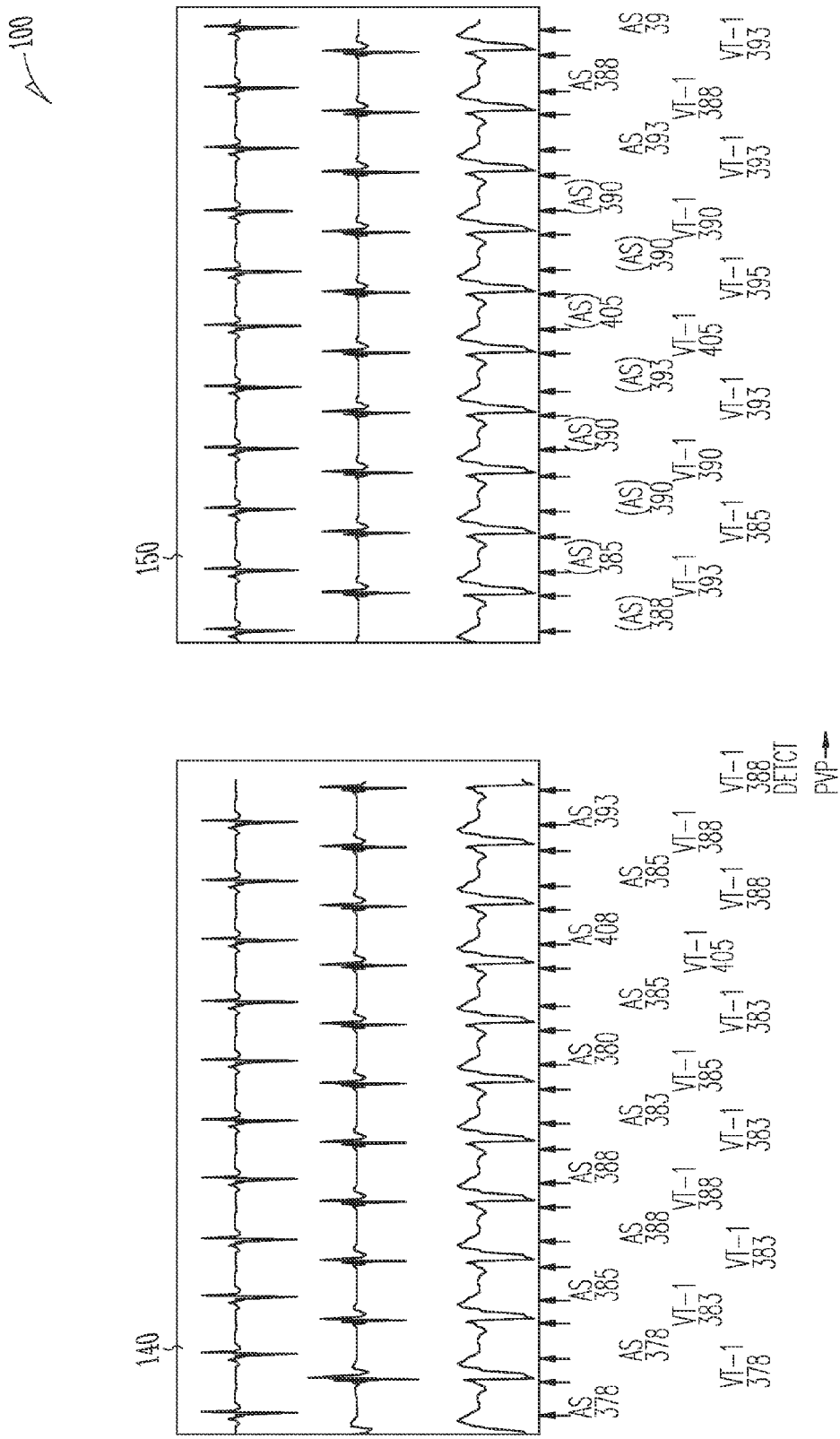

FIGS. 1A-1B are example reproductions of multiple timeline segments of electrogram (EGM) data illustrating an arrhythmia episode. In an example, an illustration 100 includes an EGM onset timeline segment 130, a pre-episode EGM timeline segment 140, and a post-episode timeline segment EGM 150. Each of the illustrated EGM timeline segments includes a graphical portion 110 depicting the sensed and evoked depolarizations, which represent electrical signals indicating heart function. In this example, each EGM time segment also includes a variety of device markers 120 noted along the bottom of the graphical display 120. In this example, the device markers are time synchronized to the graphical EGM data. Device markers can include indicators of operations such as atrial sense (AS), right ventricle sense (VS, VT, VF), right ventricle pace (VP), left ventricle sense (LVS), left ventricle pace (LVP), noise inhibited pace, persistent noise, post ventricular atrial refractory period (PVARP) extension, and atrial tachyarrhythmia response (ATR), among others. The EGM timeline data allows a physician to see detail regarding a patient's heart function over a period of time. Being able to visualize the depolarization morphologies can provide the physician valuable information for further treatment and CRM device programming.

Figure 2:
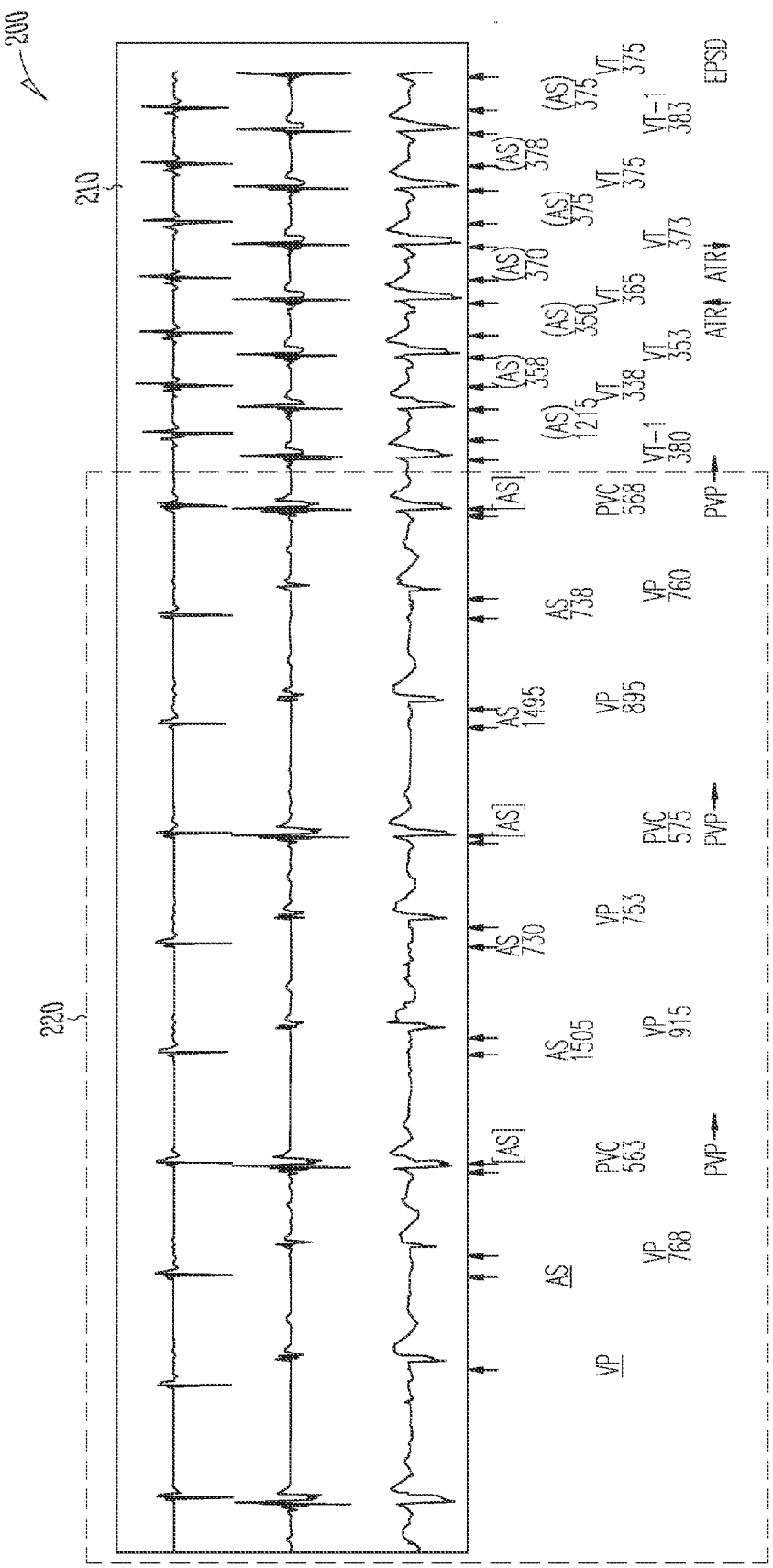
FIG. 2 is a reproduction of an example of one timeline segment of electrogram (EGM) data illustrating an arrhythmia episode including the onset of the episode.

FIG. 2 is a reproduction of one timeline segment of electrogram (EGM) data illustrating a tachyarrhythmia episode including the onset of the episode. In this example, the illustration 200 includes an EGM timeline segment 210 with a portion highlighted indicating the episode onset 220. Because storing EGM timeline data can use a considerable amount of memory, approximately 1.7 KB per cardiac cycle (at 60 BPM), the present inventors have recognized that methods of capturing only the time segments of interest to the physician are particularly beneficial. Although the operation of the implanted device can be monitored with an external programmer some of arrhythmia episodes or other occurrences of interest only occur intermittently or under special circumstances not reproducible in the physician's office. In certain situations it can be extremely useful for the physician to observe data recorded at the onset of an episode, such as for a tachyarrhythmia episode. Therefore, a method of capturing data based on events predictive of a future episode or indicative of an onset of a future episode, and then associating the onset timeline EGM data, such as 220, with actual episode data captured later can provide clinically useful output.

Figure 3:
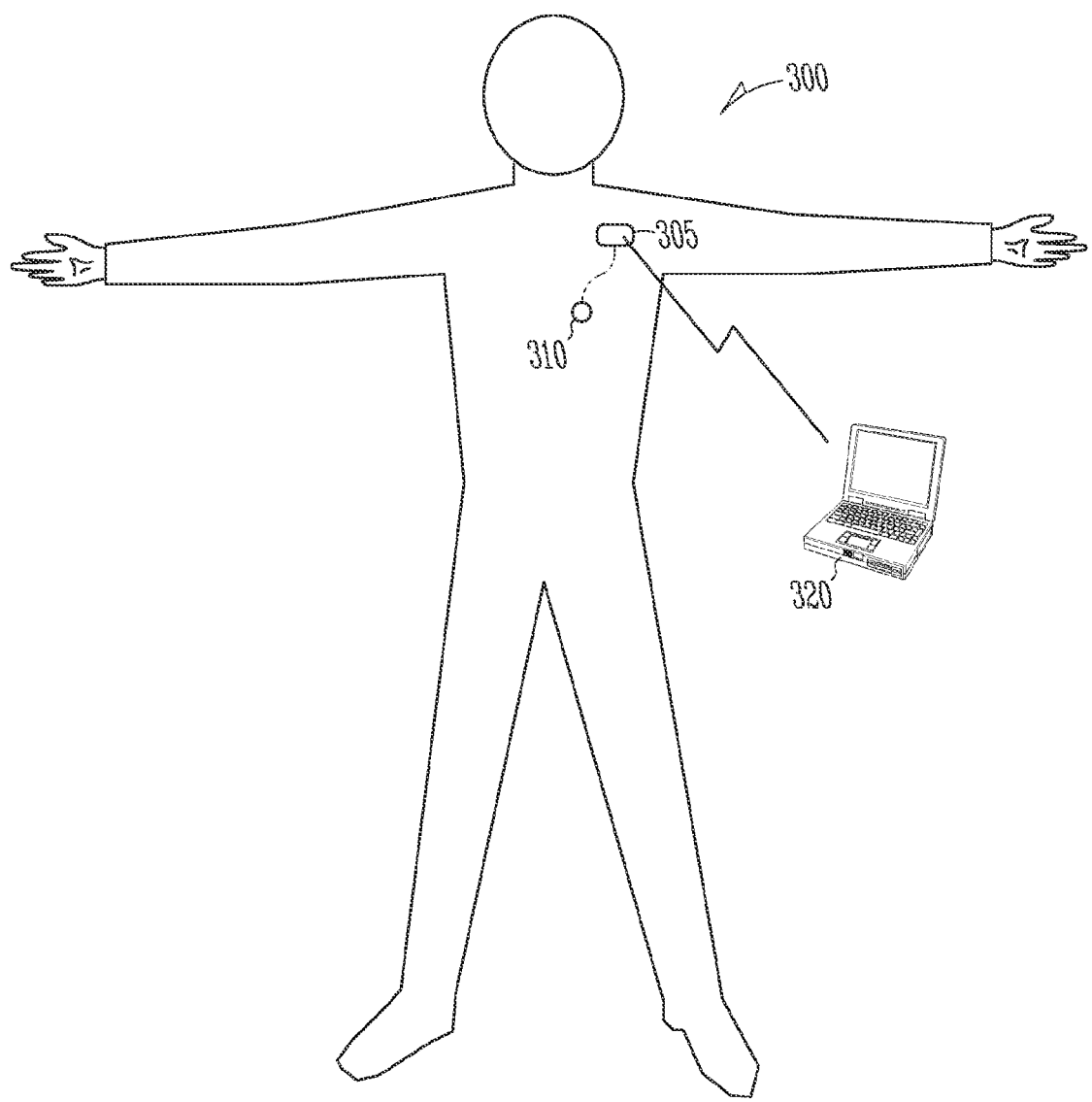
FIG. 3 is block diagram illustrating an example of an implantable cardiac rhythm management system communicatively coupled to an external programming and diagnostic device.

FIG. 3 is a block diagram illustrating an example of an implantable cardiac rhythm management system communicatively coupled to an external programming and diagnostic device. In this example, the system 300 can include an implantable medical device (IMD) 305, a physiological data sensor 310, and an external device 320. In an example, the IMD 305 can include a cardiac rhythm management (CRM) device used to provide cardiac rhythm therapy to a patient's heart. In an example, the physiological data sensor 310 can be used to detect EGM data, such as including both sensed and evoked response depolarization information. In another example, the physiological data sensor 310 can be used to monitor one or more other physiological parameters related to cardiac operations, such as heart rate, respiration rate, or blood pressure, among others. In some examples, multiple physiological data monitors can be employed to monitor multiple relevant physiological parameters.

The external device 320 can be used for programming the IMD 305 or displaying data obtained from the IMD 305. In an example, the external device can include a personal computer, such as a laptop, configured to communicate with the IMD 305. In an example, the external device communicates via a hardwired communication link with the IMD 305. In another example, the external device 320 communicates over a wireless communication link with the IMD 305. In an example, the external device 320 can receive data from the IMD 305 and display that, such as on a computer display. The external device 320 can also calculate one or more statistics or perform additional analysis to assist a physician, technician, engineer, or other user in monitoring or diagnosing the patient or in adjusting one or more operating parameters of the IMD 305. An example of additional analysis can include creating counters for various device stored pathological episodes, such as atrial tachyarrhythmia response (ATR), treated and non-treated ventricular tachyarrhythmia episodes.

Figure 4:
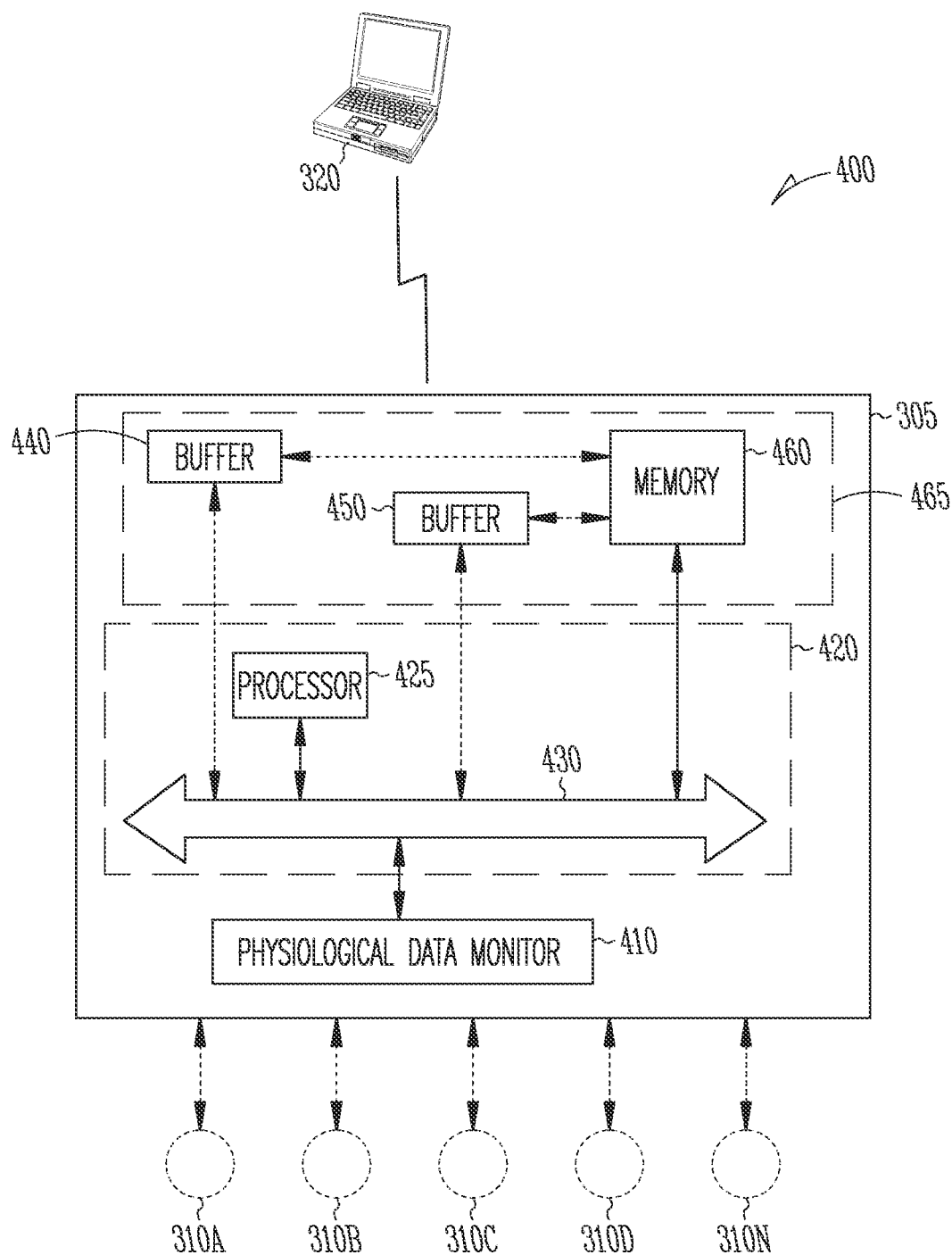
FIG. 4 is a block diagram illustrating an example of an implantable cardiac rhythm management system configured to enable adaptive event storage.

FIG. 4 is a block diagram illustrating an example of an implantable cardiac rhythm management system configured to enable adaptive event storage. In an example, a system 400 can include an implantable medical device 305, one or more physiological data sensors 310A, 310B, . . . , 310N (collectively hereinafter referred to as 310), and an external device 320. In an example of the system 400, the IMD 305 can include a physiological data monitor 410, a processor 420, and a memory 465. In some examples, the processor 420 can include a processor 425 and a communication bus 430. In an example, the communication bus 430 can enable communication between the physiological data monitor 410, the processor 425 and the memory 465. In certain examples, the memory 465 can include a main memory 460, a first buffer 440 and a second buffer 450. In an example, the first buffer 440 can include a rolling data buffer. In this example, the rolling data buffer 440 can be configured as a first-in, first-out (FIFO) memory device. In certain examples, the second data buffer 450 can include a static memory buffer configured to capture a time segment of data from either the processor or the physiological data monitor. In an alternative example, the second data buffer 450 can be configured as a FIFO memory device, similar to the rolling data buffer 440. In order to save valuable storage space, various data compression techniques can be used within the data buffers 440, 450 as well as the memory 460. In some examples, different data compression techniques can be used within each of the data buffers 440, 450 and the memory 460.

In an example, the communication bus 430 or the processor 420 can be capable of communicating directly with any combination of the first data buffer 440, the second data buffer 450, the main memory 460, the memory 465, or the physiological data monitor 410. In certain examples, the communications bus 430 can be eliminated in favor of direct communication connection between the other device components.

In an example, the physiological data monitor 410 can receive data from one or more physiological data sensors 310. In certain examples, the physiological data sensors 310 can include sensors implanted within the patient's body, also referred to as internal sensors. In other examples, the physiological data sensor(s) 310 can include ambulatory or other external sensors such as worn or carried by the patient or adhered the a patient's skin or worn against a patient's skin. In some examples, the physiological data sensors 310 can include both external and internal sensors. In an example, the physiological data sensors 310 can include one or more of a heart sound sensor, a blood pressure sensor, a posture sensor, a respiratory sensor, an activity sensor, or a chemical sensor.

In this example, the physiological data monitor 410 can be configured to receive data from any or all of the sensors and to communicate the received data such as to other portions of the IMD 305 or to an external interface device.

Once received, the monitored physiological data can be transferred to the processor 425 or stored directly in one or more of the first data buffer 440, the second data buffer 450, or the main memory 460. In this example, any of the first data buffer 440, the second data buffer 450, or the main memory 460 can be accessed by the external device 320. In some examples, the memory 465 can be accessible to the external device 320 over a communications link. As discussed above, the communications link between the external device 320 and the IMD 305 can be either wired or wireless.

Figure 5:
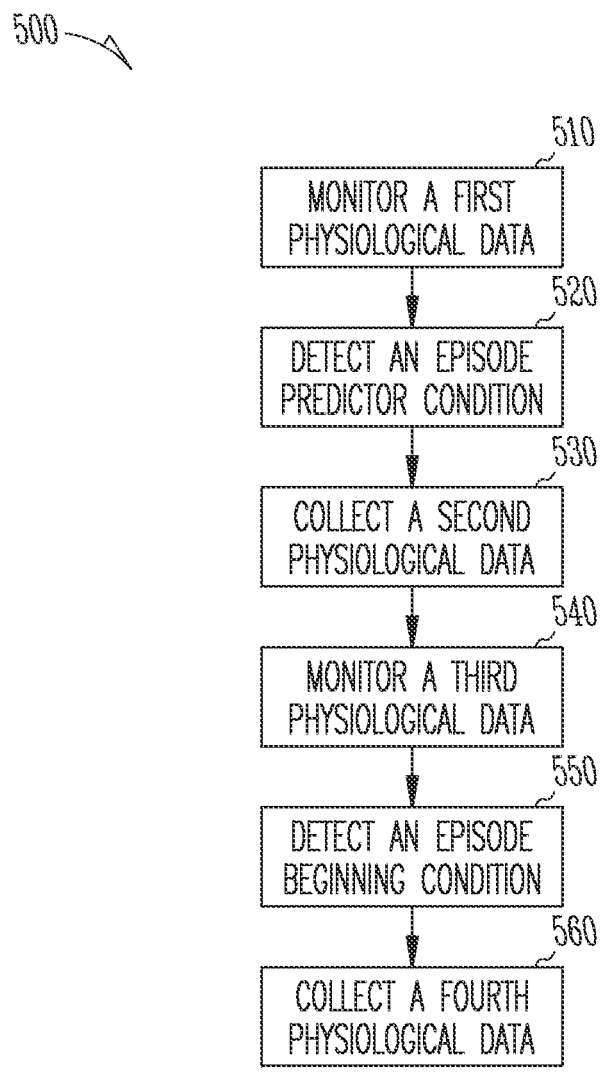
FIG. 5 is a flowchart illustrating an example of a method of adaptive event storage in an implantable CRM device.

FIG. 5 is a flowchart illustrating an example of a method of adaptive event storage such as can be used in an implantable CRM device. In an example, a method 500 includes monitoring a first physiological data parameter 510, detecting an episode predictor condition 520, collecting a second physiological data parameter 530, monitoring a third physiological data parameter 540, detecting an episode beginning condition 550, and collecting a fourth physiological data parameter 560.

At 510, in an example, the method 500 begins with the physiological data monitor 410 monitoring a first physiological data parameter, such as heart rate or respiration rate. In an example, the physiological data monitor can use one or more of the physiological data sensors 310 to obtain the monitored parameter from the patient.

At 520, using the monitored first physiological data parameter, the method 500 continues by detecting an episode predictor condition. The episode predictor condition can be any test or threshold or the like indicative of a possible future episode of interest for monitoring. In an example, an episode predictor condition of a future tachyarrhythmia episode can be an elevated heart rate that exceeds a tachyarrhythmia prediction threshold value, but is below an actual tachyarrhythmia detection threshold value. For example, if the tachyarrhythmia detection heart rate zone begins at 150 bpm (beats per minute), such that a heart rhythm exceeding this rate is declared a tachyarrhythmia, then an episode predictor condition can be set at 120 bpm, such as to help collect information about the onset of a possible future tachyarrhythmia episode, as described herein.

Although this example has focused on heart rate, the episode predictor condition can be triggered off any number of physiological data parameters or statistics kept by the IMD 305. Some example physiological data parameters can include heart rate, respiration rate, electrogram morphology, blood pressure, atrial versus ventricular heart rate, or heart rate stability. In certain examples, the episode predictor condition can include a combination of multiple physiological data parameters. In some examples, the episode predictor condition can be configured to trigger when the rate of change of a monitored physiological data parameter meets a specified test. In an example, meeting the specified test can include exceeding a threshold rate of change, for example, a rapid acceleration in heart rate. In these examples, the IMD 305 can also be configured to qualify or disregard a rapid rate of change if physical exertion is also detected. In an example, the episode predictor condition can be programmed by a physician, allowing the physician the ability to target certain parameters or conditions for data collection. When programmed appropriately, the episode predictor condition can allow the IMD 305 to collect and store data including the actual onset of a future episode, such as the actual onset of a future tachyarrhythmia episode, for example.

At 530, the method 500 continues, such as by collecting a second physiological data parameter from one or more of the physiological data sensors 310. In an example, the second physiological data parameter can be collected by the physiological data monitor 410 and stored in the memory 465. In certain examples, the second physiological data parameter can be stored in a data buffer 440. In an example, the data buffer 440 can be a static data buffer capable of holding a fixed amount of physiological data before and after a certain time. For example, when the episode predictor condition is detected, the physiological data monitor 410 can be instructed to collect the next ten seconds of data, which can then be stored in the static data buffer 440, such as for future export or analysis. The amount of data stored in the static data buffer 440 by the physiological data monitor 410 can be configured, and can be limited by the size of the memory dedicated to the static data buffer 440. In another example, the data buffer 440 can be a data buffer capable of holding a fixed amount of physiological data before and after a certain time. In this example, when the episode predictor condition is detected, the data buffer 440 can retain some portion of data collected from the physiological data monitor 410 before the episode predictor condition and some portion of data collected after the episode predictor condition.

At 540, the method 500 next monitors a third physiological data parameter. In an example, the third physiological data parameter can be monitored by the physiological data monitor 410.

At 550, the method 500 can use the monitored third physiological data parameter to detect an episode beginning condition. In an example, the episode beginning condition can represent an actual episode, such as a tachyarrhythmia. The detection of an episode beginning condition can be triggered by one or many different events, an example can include a rapid heart rate (e.g., within a tachyarrhythmia rate zone, e.g., exceeding 150 bpm) or a sudden increase in respiration without a corresponding detection of physical exertion.

At 560, the IMD 305 can respond to the detected episode beginning condition, such as by collecting a fourth physiological data parameter of interest during the actual episode. In an example, the episode beginning condition triggers the collection of the fourth physiological data parameter by the physiological data monitor 410. The collected data can be stored in the memory 465 such as for future export to an external programming device 320 or analysis by the processor 425. In certain examples, the fourth physiological data parameter can be collected in a rolling data buffer 250. The rolling data buffer 250 can be configured to store a fixed amount of data such as in a first in, first out (FIFO) manner. The FIFO configuration allows the IMD 305 to continually maintain a certain specified time segment of the fourth physiological data parameter. For example, if the FIFO buffer 450 is specified to be capable of storing 30 seconds of EGM timeline data, at any given moment in time during which the FIFO buffer 450 is receiving data, the IMD 305 has access to the past 30 seconds of EGM timeline data. Storing data in a rolling buffer provides some ability to capture past events, within the specified length of the buffer. In an example, detecting the episode beginning condition can trigger the IMD 305 to store the current contents of the rolling data buffer 450 into the memory 460. In an example, the detection of the episode beginning condition can trigger the IMD 305 to collect an additional specified time period of data in the rolling data buffer before storing the contents into the memory 460. For instance, if the rolling data buffer is capable of storing thirty (30) second of data, the IMD 305 can be configured to collect twenty (20) seconds of data after the episode beginning condition is detected, resulting in ten (10) seconds of data before the episode beginning condition and twenty (20) seconds of data after detection to be available for later storage in the memory 460. Additionally, the IMD 305 can be configured to store more data after the episode beginning condition is detected by repeatedly storing the contents of the rolling data buffer 450 in the memory 460. In an example, the rolling data buffer 450 can be capable of storing ten (10) seconds of data. In this example, when the episode beginning condition is detected, the past ten seconds of data stored in the rolling buffer 450 can be stored to the memory 460. Subsequently, two additional ten second segments of data stored in the rolling data buffer can be stored in the memory 460. Thus, thirty seconds of episode data can be saved to the memory 460 using a rolling data buffer 450 capable of storing just ten seconds of data. In this example, the size of the rolling data buffer 450 determines the length of time prior to detection of the episode beginning condition that can be retained.

In some examples, the IMD 305 can have multiple triggering conditions configured, and the IMD 305 can also store an indication of which triggering condition caused a particular storage event. Additional statistical information regarding the current episode can be stored, such as the actual percentage of paced ventricular beats or average PR interval for a specified time interval preceding the episode beginning condition. Also, additional data regarding the condition of the patient can be useful in diagnosing the circumstances or symptoms associated with the data stored about the episode. Therefore the IMD 305 can also store items such as atrial rate, ventricular rate, physical activity or exertion level, respiration rate, autonomic balance, date, or time. In addition to the data stored when a triggering condition is met, the system can also continuously store information regarding one or more of the triggering parameters. In an example, the IMD 305 can continuously store the percentage of time during which a pacing or other therapy is being delivered. This data can then be displayed as a trend over time.

Figure 6:
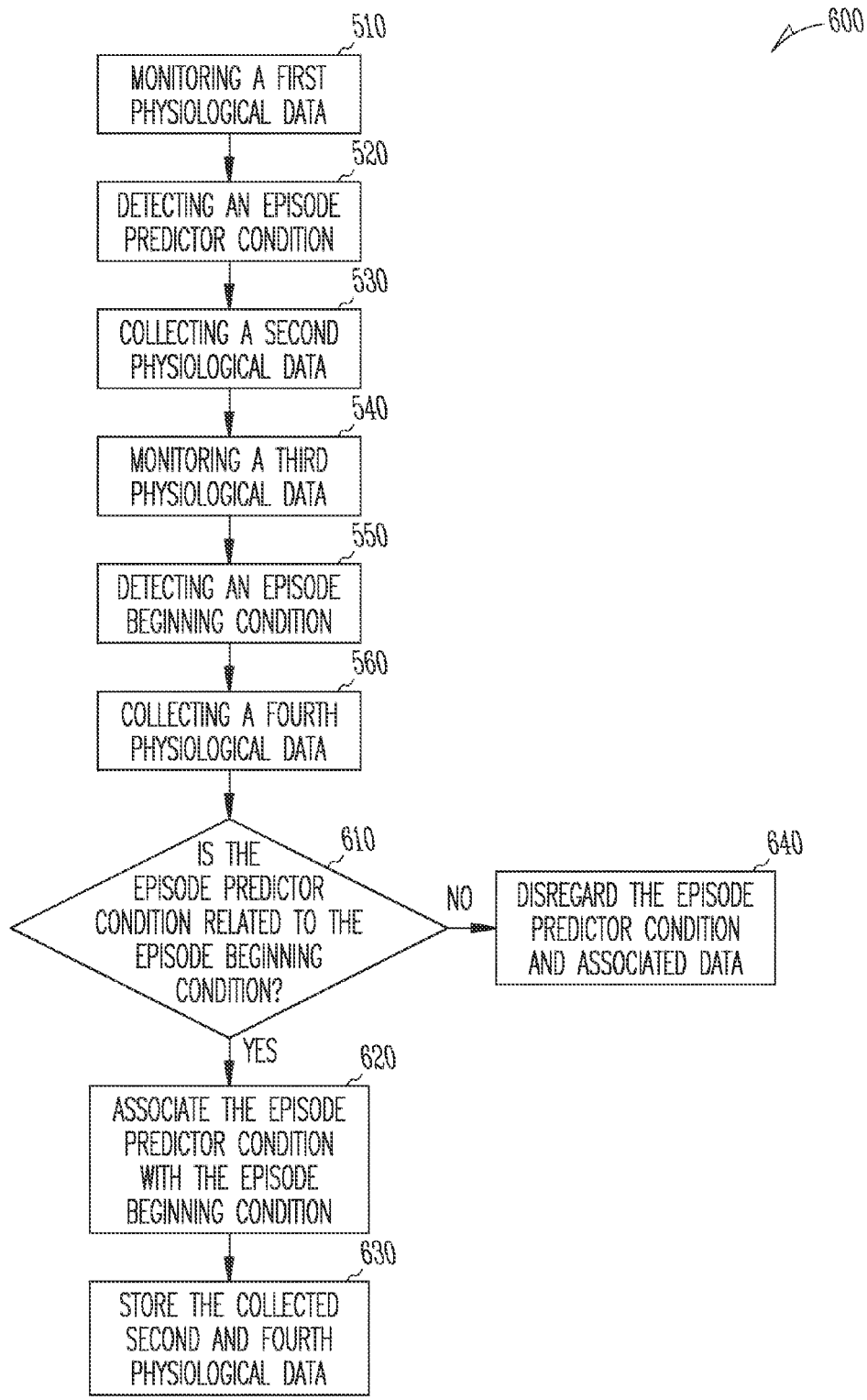
FIG. 6 is a flowchart illustrating an example of a method of adaptive event storage in an implantable CRM device.

FIG. 6 is a flowchart illustrating an example of a method of adaptive event storage in an implantable CRM device. In this example, a method 600 can build on the method 500 such as by including additional operations of determining whether the episode predictor condition is related to the episode beginning condition 610, associating the episode predictor condition with the episode beginning condition 620, and storing the collected second and fourth physiological data 630, such as in association with each other. Method 600 can address the potential situation in which the episode predictor condition was met, but the episode predictor condition was not predictive of an actual later episode. Whether the episode predictor condition and the episode beginning condition are indeed associated with each other (e.g., the same episode) can be determined such as based on one or more factors such as time between the episode predictor and the episode beginning conditions, the continued presence of the episode predictor condition, or correlation with one or more other monitored physiological data parameters. Additionally, whether the episode predictor and episode beginning conditions are indeed associated can also be determined using a combination of factors, such as a time period between the episode predictor and the episode beginning conditions in combination with information about the continued presence or absence of the episode predictor condition. Some examples of potential techniques for determining whether the episode predictor condition and the episode beginning condition are actually associated with the same episode are illustrated in FIGS. 7A-7C and 8A-8C.

Figure 7A:
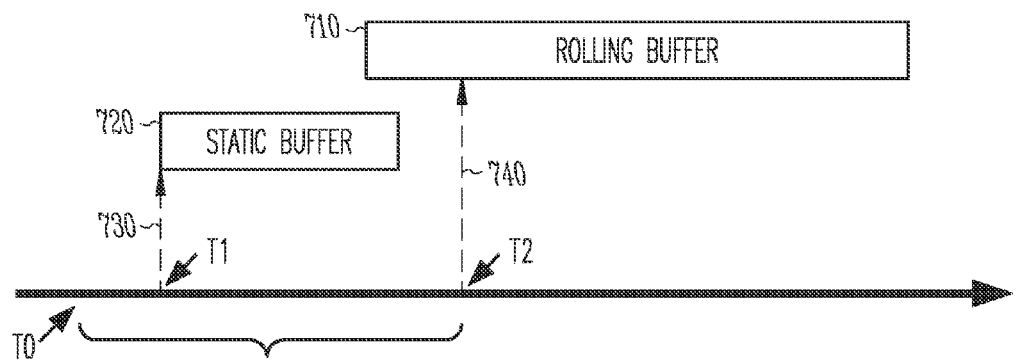
FIGS. 7A-7C are timeline diagrams illustrating an example of a method of associating the episode predictor condition with the episode beginning condition.
Figure 7B:
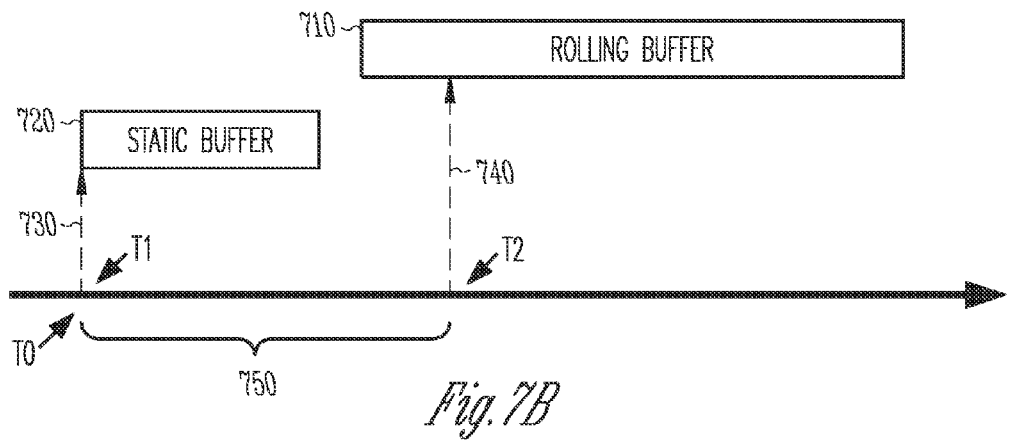
Figure 7C:
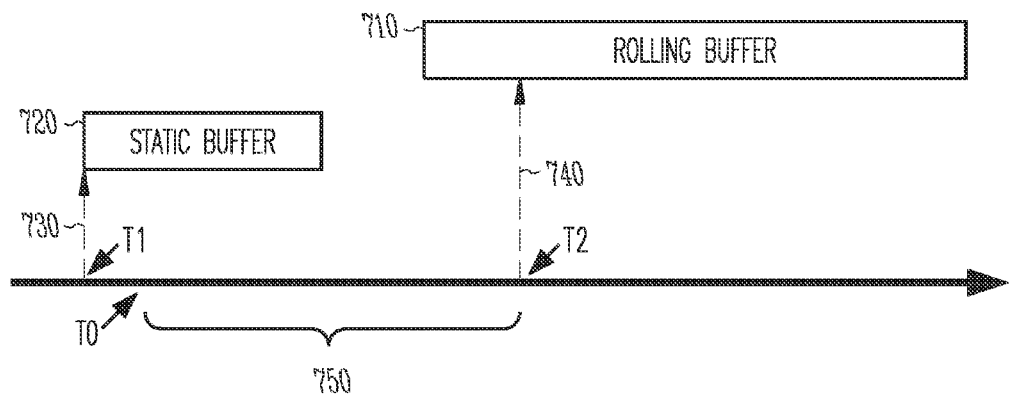

FIGS. 7A-7C are timeline diagrams illustrating an example of a method of associating the episode predictor condition with the episode beginning condition. FIG. 7A illustrates a rolling buffer 710, a static buffer 720, an episode predictor condition 730, an episode beginning condition 740, and a specified time period 750. Similar elements can be found in FIG. 7B and FIG. 7C, which depict examples of different variations of the scenario depicted by FIG. 7A. These figures illustrate an example of associating the episode predictor condition 730 and the episode beginning condition 740 using the time period 750. In each of these figures, the episode predictive condition is detected at time T1 and the episode beginning condition is detected at time T2 . Also shown in each figure is the specified time period 750 running from T2 back to T0. The time T0 represents the earliest point in time that T1 can occur and still have the episode predictive condition 730 be associated with the episode beginning condition 740, in these examples.

FIG. 7A illustrates an example in which the episode predictive condition 720 is detected well after time T0. Therefore, in this example, the episode predictive condition 730 would be associated with the episode beginning condition 740. FIG. 7B illustrates a boundary condition, in which the episode predictive condition 730 occurs at T0 (T0 equals T1 ). Whether this boundary condition would associate the two conditions depends on how the IMD 305 is programmed. For example, if the IMD 305 is programmed such that T1 must be greater than T0 (i.e. closer to T 2) then the episode predictive condition 730 would not be associated with the episode beginning condition 740. However, if the IMD 305 is programmed to allow T1 to equal T0, then the two conditions would be associated. FIG. 7C illustrates an example where the two conditions would not be associated. In FIG. 7C the episode predictive condition clearly occurs prior in time to T0 and is outside the time period 750 used to make the association. Thus, in a tachyarrhythmia episode example, in which onset data is stored in the static buffer 720, and tachyarrhythmia episode data is stored in the rolling buffer 710, the tachyarrhythmia onset data can be stored in association with the tachyarrhythmia episode data for the situations shown in FIGS. 7A-7B, and not for the situation shown in FIG. 7C.

In an example not specifically illustrated by FIGS. 7A-7C, the episode predictor condition 730 can be associated with the episode beginning condition if any portion of the data stored in the static buffer 720 was recorded within time period 750. In this example, all three scenarios depicted by FIGS. 7A-7C would result in the data stored in the static buffer 720 being associated with the data stored in the rolling buffer 710.

Figure 8A:
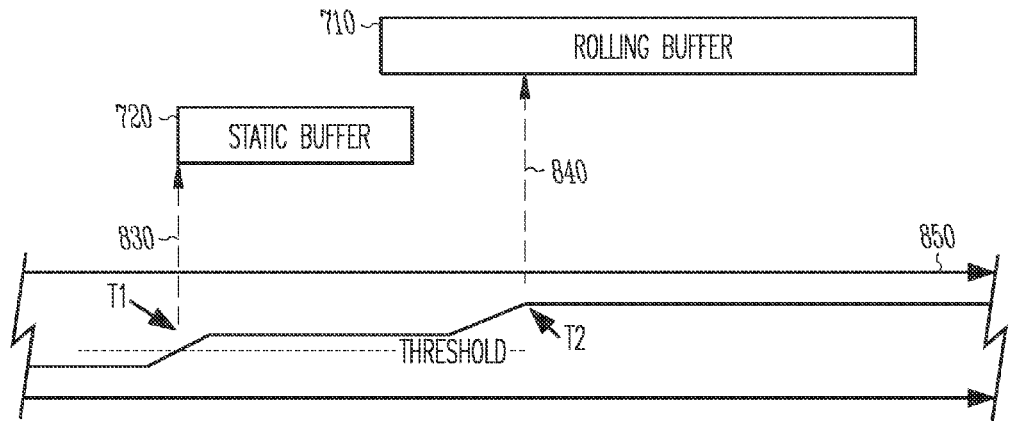
FIGS. 8A-8D are timeline diagrams illustrating an example of a method of associating the episode predictor condition with the episode beginning condition.
Figure 8B:
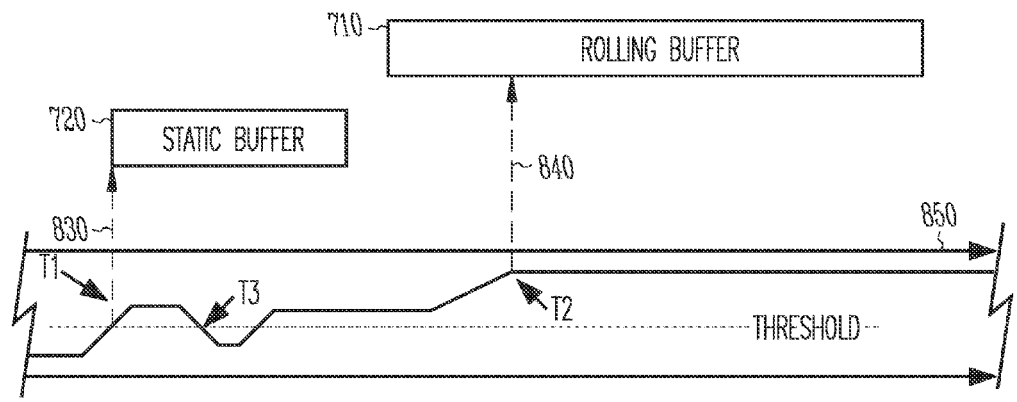
Figure 8C:
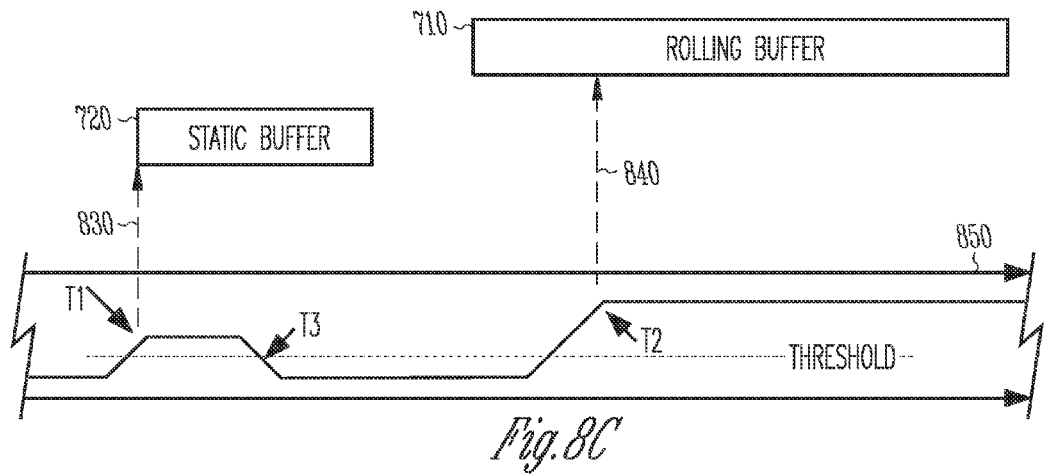

FIGS. 8A-8C are timeline diagrams illustrating an example of a method of associating the episode predictor condition with the episode beginning condition. FIGS. 8A-8C each include illustrations of a rolling buffer 710, a static buffer 720, an episode predictive condition 830, an episode beginning condition 840, and a strip chart 850 depicting a time segment of recorded physiological data. These figures illustrate associating the episode predictor condition 830 and the episode beginning condition 840 based on the continued (e.g., "sustained") presence of the episode predictor condition 830 between the time the episode predictor condition is detected at time T1 until the episode beginning condition is detected at time T2.

FIG. 8A depicts an example where the episode predictor condition 830 will be associated with the episode beginning condition 840 based on the continued presence of a physiological condition which led to detection of the episode predictor condition 830. In this example, the strip chart 850 depicts a physiological parameter, such as heart rate or respiration rate. At time T1, the strip chart depicts the physiological parameter jumping up above an episode predictive threshold condition. Continuing to the right, the strip chart 850 depicts the physiological parameter remaining above the episode predictive threshold condition until T2 when the episode beginning condition 840 is detected. Thus, this example depicts a situation where the episode predictor condition can be associated with the episode beginning condition.

FIG. 8B depicts an example where the episode predictor condition 830 can be associated with the episode beginning condition 840, such as if the episode predictive condition 830 need only be substantially present until the episode beginning condition 840 is detected. Once again the strip chart 850 depicts a physiological parameter ramping up above the episode predictive threshold condition 830 at time T1. However, unlike the scenario depicted in FIG. 8A, the physiological parameter falls below the episode predictive threshold at time T3 for a short period of time. In an example, anytime the episode predictive condition 830 fails to persist continually until the episode beginning condition 840 is detected, the episode predictive condition and the episode beginning conditions can be deemed unassociated. In another example, the episode predictive condition 830 need only be substantially present until the episode beginning condition 840 is detected for these two conditions to be associated. In this example, a short absence of the episode predictive condition 830, as illustrated in FIG. 8B, would not prevent association of these two conditions. The exact degree or time period of an absence of the episode predictive condition 830 can be configured depending on the situation, the physiological data being monitored, or the diagnostic purpose of the data collection. The exact degree or time period of an absence of the episode predictive condition 830 can be configured using an absolute indication of the time of absence, or a relative indication (e.g., a percentage) of a sum total of periods of absence relative to an elapsed time since the initial detection of the episode predictive condition. In an example, FIG. 8B can be described as the episode predictive condition having some level of hysteresis.

FIG. 8C depicts an example in which the episode predictor condition 830 will not be associated with the episode beginning condition 840 based on a lack of persistence of the episode predictor condition 830 until detection of the episode beginning condition 840. The strip chart 850 depicts a physiological parameter triggering detection of the episode predictive condition 830 at time T1 and later triggering detection of the episode beginning condition 840 at time T2. However, the strip chart 850 also depicts the physiological parameter dropping below the episode predictive condition 830 shortly after time T1 at time T3. In this example, the physiological parameter does not re-trigger detection of the episode predictive condition 830 between time T3 and time T2 when detection of the episode beginning condition occurs. In this example, the episode predictive condition 830 would not be associated with the episode beginning condition 840.

Figure 8D:
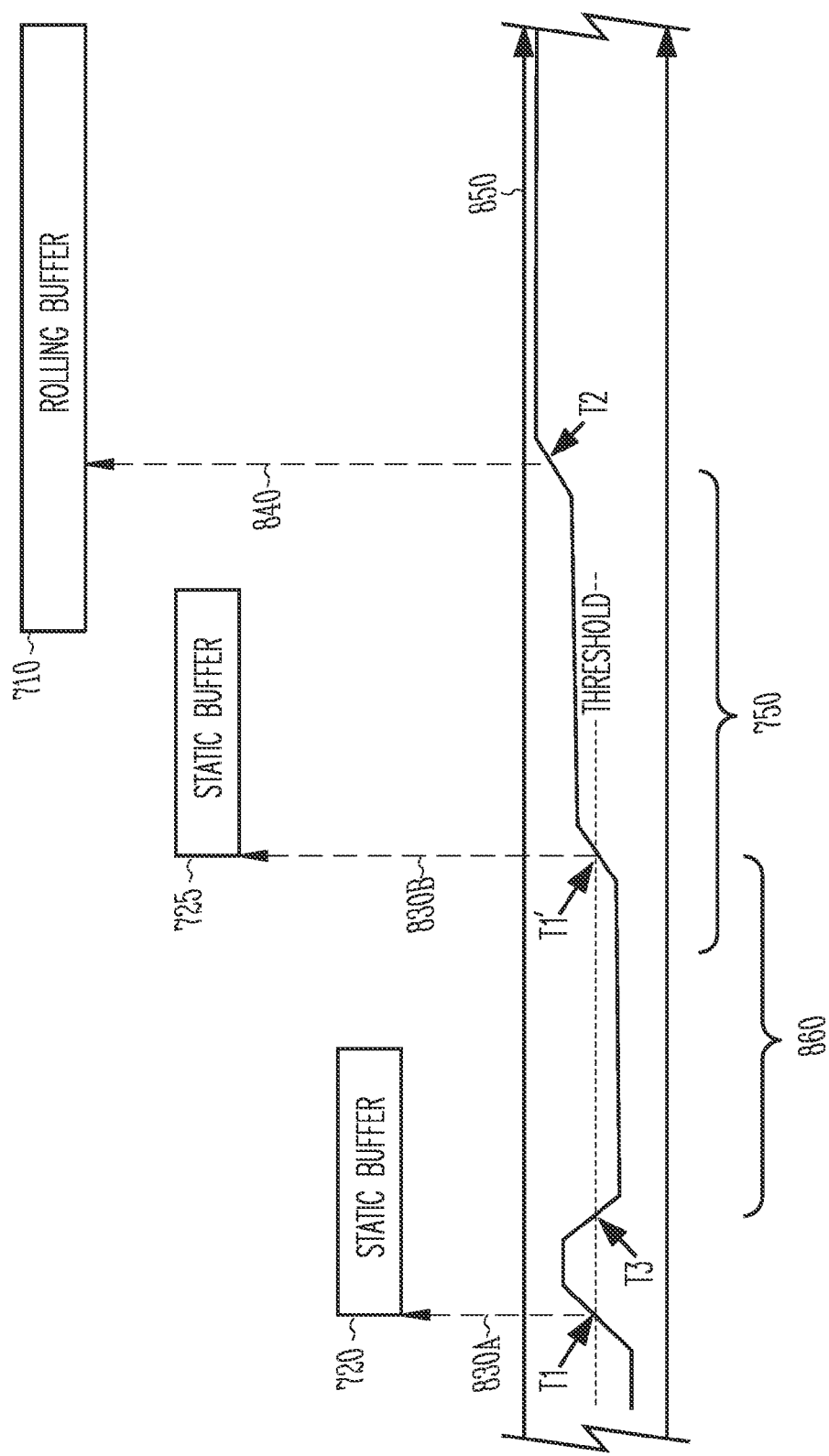

FIG. 8D depicts an example in which the episode predictor condition 830A, 830B occurs multiple times prior to detection of the episode beginning condition 840. In this example, the strip chart 850 depicts a physiological parameter triggering detection of the episode predictive condition 830A, 830B at time T1 and time T1'. In an example, static buffer 720 triggered on the detection of the first episode predictive condition 830A can be discarded, due to the length of time 860 in which the physiological parameter was below the threshold. If the first static buffer 720 is disregarded, then only the second static buffer 725 will be associated with the rolling buffer 710. In another example, the time period 860 may be short enough for the dip in the physiological parameter to be disregarded, as described in FIG. 8B. This is example, the first static buffer 720 can be associated with the rolling buffer 710. In the examples illustrated by FIG. 8D, if both of the static buffers are eligible to be associated with the rolling buffer, according to the rule described above in reference to FIGS. 7A-7C and 8A-8C, then one or both of the static buffers 720, 725 can be associated with the rolling buffer 710. In an example, the earliest in time static buffer, in this case static buffer 720, can be associated with the rolling buffer 710. In another example, only the static buffers that occur within a specified time period 750 can be associated with the rolling buffer 710. As illustrated by FIG. 8D, limiting association to static buffers within time period 750 would eliminate static buffer 720. In yet another example, the most recent in time, in relation to the episode beginning condition 840, static buffer 725 can be associated with the rolling buffer 710.

Returning to FIG. 6 and method 600, if it is determined that the episode predictor condition is related to the episode beginning condition the conditions can then be associated at 620. Association of the episode predictive condition and the episode beginning condition can result in the collected second and fourth physiological data to be stored as related information. For example, the second physiological data collected in the static buffer 440 can be stored in the memory 460 as being associated with the fourth physiological data collected in the rolling buffer 450. Associating this data allows a physician to observe the onset information from the static buffer 440 in relationship to the actual episode data from the rolling buffer 450, providing a more complete picture of the episode.

At 610, if it is determined that the episode predictive condition is not related to the episode beginning condition, then data collected in response to the episode predictive condition can be discarded. In an example where the episode predictive condition is not actually predictive of a later related episode, the collected data is then not truly indicative of an onset of an episode and thus is not of interest to a physician for diagnostic purposes. In some examples, the IMD 305 can be configured to store non-associated data collected as a result of detection of an episode predictive condition. In these examples, the physician may be interested in the data regardless of whether or not a subsequent episode occurred, or a device engineer may be interested in what sort of data predicts but fails to lead to an actual later episode.

Figure 9:
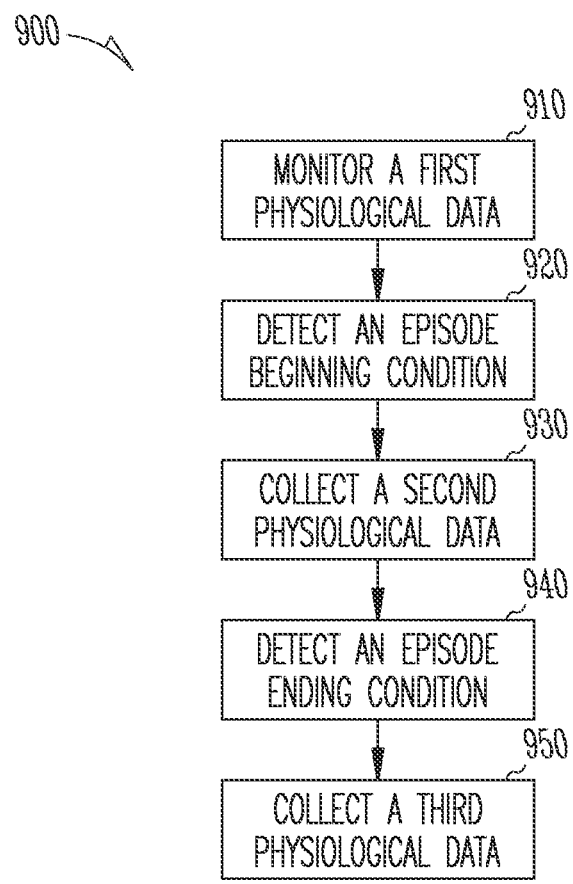
FIG. 9 is a flowchart illustrating an example of a method of post episode adaptive event storage in an implantable CRM device.

FIG. 9 is a flowchart illustrating an example of a method of post episode adaptive event storage in an implantable CRM device. In an example, a method 900 can include monitoring a first physiological data parameter 910, detecting an episode beginning condition 920, collecting a second physiological data parameter 930, detecting an episode ending condition 940, and collecting a third physiological data parameter 950.

At 910, in an example, the method 900 begins with the physiological data monitor 410 monitoring a first physiological data parameter, such as heart rate, respiration rate, or EGM morphology. In this example, the physiological data monitor can use one or more of the physiological data sensors 310 to obtain the monitored data from the patient.

At 920, using the monitored first physiological data parameter, the method 900 continues by detecting an episode beginning condition. As discussed in detail above, the episode beginning condition can be detected through the processor 425 interpreting one or more physiological data parameters. In this example, the episode beginning condition can be detected by the processor 425 such as by determining if the monitored first physiological data parameter meets some specified test. Examples of the specified test can include exceeding a threshold, determining that multiple consecutive measurements exceed a threshold, detecting a prolonged absence of a monitored physiological data parameter, or some combination of these factors.

At 930, once the episode beginning condition is detected at 920, the method 900 continues by collecting a time segment of the second physiological data parameter. In an example, the IMD 305 collects, via the physiological data monitor 410, a time segment of EGM data and stores it in memory 465. In another example, the IMD 3005 triggers the storage of a time segment of second physiological data parameter currently contained in a rolling buffer 450.

At 940, in this example, the method 900 continues by detecting an episode ending condition at 940. The episode ending condition can be indicative of the ending of the present episode. In an example, the episode ending condition can be detected when the IMD 305 delivers a therapy, such as an electrostimulation. In certain examples, the episode ending condition can be detected when one or more of the monitored physiological parameters meets a specified test. Once an episode ending condition is detected, the method 900 collects a third physiological data parameter at 950. In an example, a time segment of the third physiological data parameter can be collected and stored in the memory 465. The data collected upon detection of the episode ending condition can include heart rate, EGM data, pressure sensor data, posture sensor data, activity level data, respiratory sensor data, chemical sensor data, or device markers. The amount of data collected and subsequently stored can depend on available IMD 305 memory, such as memory 465, as well as the type of data collected. For example, a time segment of device marker data can be much more compact that a similar time segment of EGM data.

In an example, the collection of the third physiological data can be triggered immediately upon detection of the episode ending condition. In another example, the collection of the third physiological data can be triggered after a specified delay beyond the time when the episode ending condition was detected. In some examples, the specified delay depends upon the type of therapy delivered by the IMD 305. In yet another example, the collection of the third physiological data can be triggered upon detection of another physiological data parameter meeting a specified test. The specified test could include the physiological data parameter dropping below a specified threshold or the detection of multiple EGM cycles that exhibit a certain morphology. In certain examples, the collection of the third physiological data can be triggered by a combination of these factors.

Figure 10A:
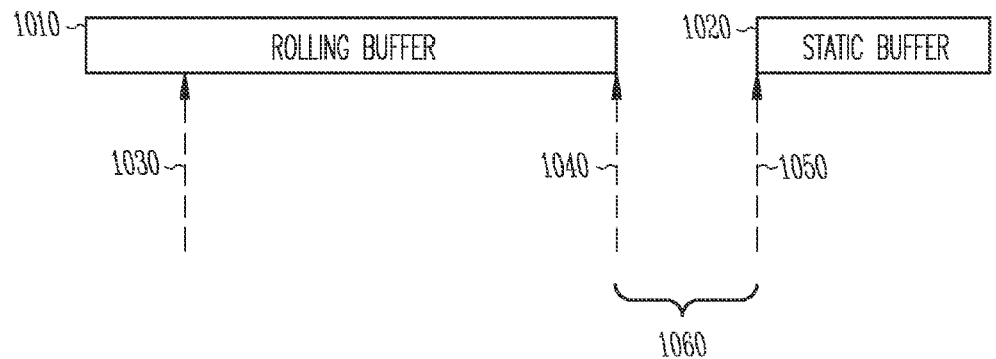
FIGS. 10A-10B are timeline diagrams illustrating examples of methods of determining when to trigger post episode event storage.
Figure 10B:
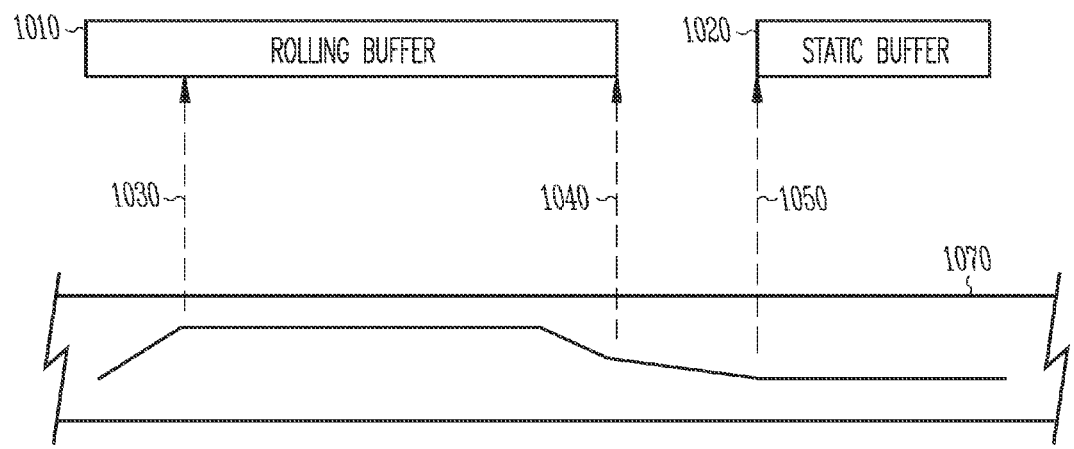

FIGS. 10A-10B are timeline diagrams illustrating examples of methods of determining when to trigger post episode event storage. FIGS. 10A-10B each include illustrations of a rolling buffer 1010, a static buffer 1020, an episode beginning condition 1030, an episode ending condition 1040, and a post episode event storage trigger 1050. These figures illustrate two examples of options for triggering physiological data collection after an episode, such as tachyarrhythmia, has occurred.

FIG. 10A is a timeline diagram illustrating an example of a method of triggering post episode event storage based on a specified time period. In this example, the time period 1060 depicts a specified time period after detection of the episode ending condition 1040. The expiration of the specified time period 1060 can trigger the post episode event storage. The specified time period 1060 can be configured based on episode type or data to be collected, among other things.

FIG. 10B is a timeline diagram illustrating an example of a method of triggering post episode event storage based on a monitored physiological parameter. In this example, the strip chart 1070 depicts a physiological parameter, such as heart rate or respiration rate. In this example, the strip chart 1070 depicts the physiological parameter (e.g., heart rate) triggering the episode beginning condition 1030, such as a tachyarrhythmia. The strip chart 1070, then illustrates an episode ending condition 1040 corresponding to a change or reduction in the monitored physiological parameter, indicating recovery from the tachyarrhythmia episode. In this example, the post event storage 1050 is not triggered until further change or reduction in the monitored physiological parameter is detected. In an example, the post event storage trigger 1050 can be delayed until the physiological parameter reaches a substantially steady state.

Post Episode Data Collection Examples:

In Example 1, a system includes an implantable medical device that includes a physiological data monitor, a processor, a rolling memory buffer, a static memory buffer, and memory. The physiological data monitor is configured to monitor one or more physiological data parameters. The processor is coupled to the physiological data monitor and configured to detect an episode beginning condition and an episode ending condition. The episode beginning condition is indicative of the beginning of a present pathological episode and can be detected using a first physiological data parameter monitored by the physiological data monitor. The episode ending condition is indicative of the ending of the present pathological episode. The rolling memory buffer is used to continually store a fixed segment of a second physiological data parameter monitored by the physiological data monitor. The static memory buffer is configured to store a time segment of a third physiological data parameter monitored by the physiological data monitor based on a triggering event associated with the detection of the episode ending condition. The memory is configured to store data retained in the rolling memory buffer when triggered by the episode beginning condition. The memory is also configured to store data retained in the static memory buffer and to associate the data retained in the static memory buffer with the data retained in the rolling memory buffer for later use by the implantable device or for output to an external device.

In Example 2, the processor of Example 1 detects the episode ending condition when the implantable medical device delivers a therapy.

In Example 3, the static memory buffer of Example 2 is triggered to store data after a specified delay beyond the time the episode ending condition is detect by the processor. In this example, the specified delay can be therapy dependent.

In Example 4, the physiological data monitor of Examples 1 can be configured to monitor a fourth physiological data parameter. In this example, the processor can be configured to detect the episode ending condition when the monitored fourth physiological data parameter meets a test.

In Example 5, the physiological data monitor of Example 4 can be configured so that at least the first and the fourth physiological data represent the same physiological characteristic, and so that the monitored physiological characteristic includes at least one of heart rate, electrogram morphology, blood pressure, blood gas, blood chemistry, respiration rate, atrial versus ventricular heart rate, or heart rate stability.

In Example 6, the physiological data monitor of any one of Examples 1-5 can be configured so that at least two of the first, second, and third physiological data represent the same physiological characteristic.

In Example 7, the physiological data monitor of any one of Examples 1-5 can be configured so that at least two of the first, second, and third physiological data represent a different physiological characteristic.

In Example 8, the physiological data monitor of any one of Examples 1-7 can be configured to monitor one or more of: an electrocardiogram sensor, a heart rate sensor, a heart sounds sensor, a pressure sensor, a blood gas sensor, an electroneurogram sensor, a posture sensor, a respiratory sensor, or a chemical sensor.

In Example 9, a method includes monitoring a first physiological data parameter, detecting an episode beginning condition, collecting a second physiological data parameter, detecting an episode ending condition, and collecting a third physiological data parameter. In this example, monitoring the first physiological data parameter is accomplished using an implantable physiological data monitor. Detecting the episode beginning condition is accomplished using the monitored first physiological data parameter. The episode beginning condition is indicative of the beginning of a present pathological episode. Collection of the second physiological data parameter is triggered by detecting the episode beginning condition. The second physiological data parameter can be associated with detection of the episode beginning condition. The episode ending condition is indicative of the ending of the present pathological episode. Collection of the third physiological data is triggered by the detection of the episode ending condition. The third physiological data parameter can be associated with the detecting of the episode ending condition.

In Example 10, the episode ending condition of Example 1 is detected when an implantable cardiac rhythm management device delivers a therapy.

In Example 11, the collecting the third physiological data of Example 10 is triggered after a specified delay beyond the time the episode ending condition is detected. In this example the specified delay can be therapy dependent.

In Example 12, the method of Example 9 can also include monitoring a fourth physiological data using the implantable physiological monitor. In this example, the episode ending condition can be detected when the monitored fourth physiological data meets a test.

In Example 13, at least the first and the fourth physiological data of Example 12 can represent the same physiological characteristic. In this example, the monitored physiological characteristic includes at least one of heart rate, electrogram morphology, blood pressure, blood gas, blood chemistry, respiration rate, atrial versus ventricular heart rate, or heart rate stability.

In Example 14, at least two of the first, second, and third physiological data parameters of any one of Examples 9-13 can represent the same physiological characteristic.

In Example 15, at least two of the first, second, and third physiological data of any one of Examples 9-13 can represent a different physiological characteristic.

Example External Device and Machine-Readable Medium

Figure 11:
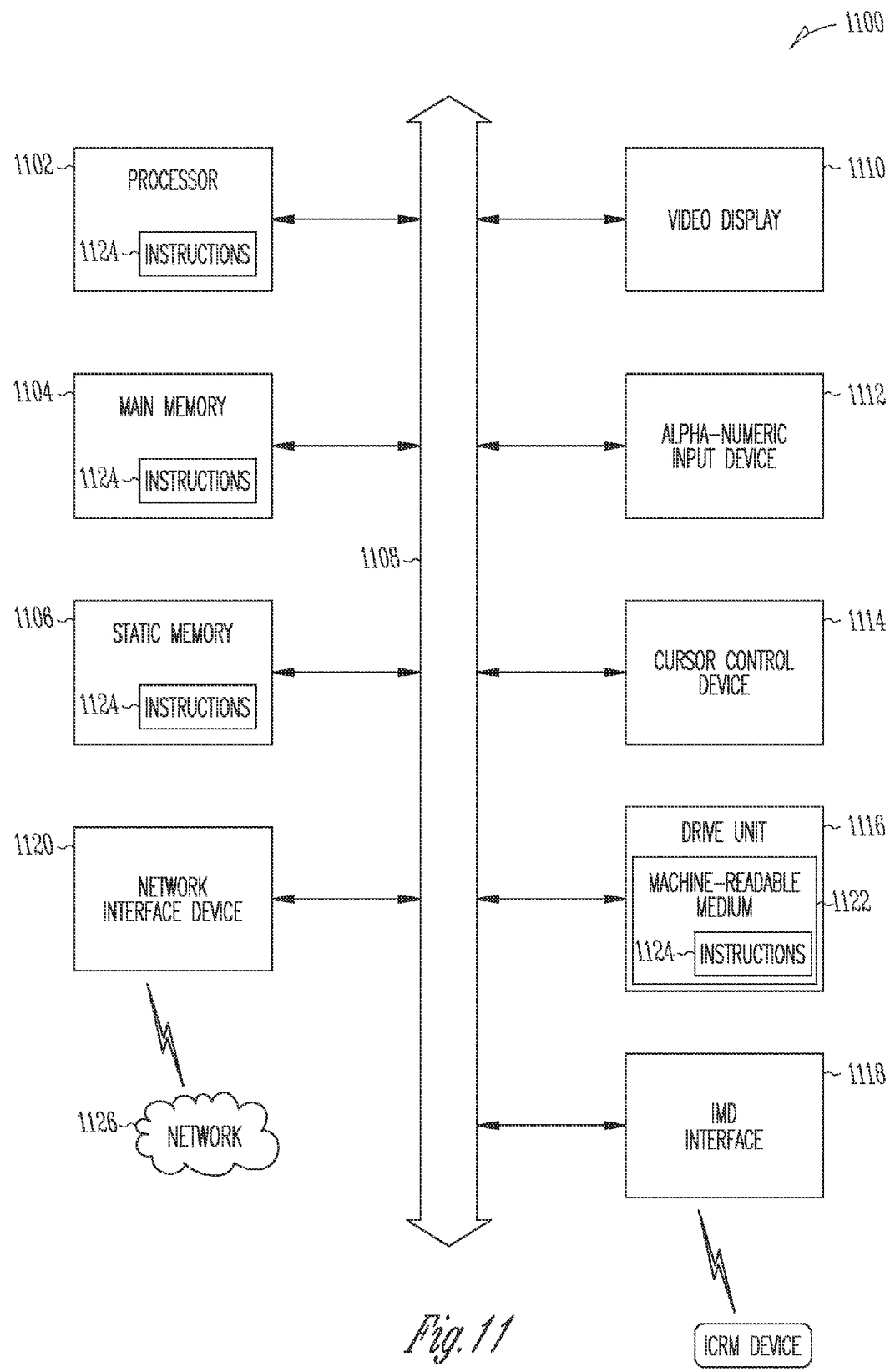
FIG. 11 is a block diagram illustrating an example of an external programming and diagnostic computer.

FIG. 11 is a block diagram illustrating an example of an external programming and diagnostic computer. The system 1100 is a machine in the example form of a computer system 1100 within which instructions, for causing the machine to assist in the performance of any one or more of the methodologies discussed herein, may be executed. In certain examples, the machine operates as a standalone device or can be connected (e.g., networked) to other machines. In a networked deployment, the machine can operate in the capacity of a server or a client machine in server-client network environment, or as a peer machine in a peer-to-peer (or distributed) network environment. The machine can be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the machine can include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 can further include a video display unit 1110 (e.g., a liquid crystal display (LCD) or a cathode ray tube (CRT)). The computer system 1100 also includes an alphanumeric input device 1112 (e.g., a keyboard), a user interface (UI) navigation device 1114 (e.g., a mouse), a disk drive unit 1116, an implantable medical device interface 1118, and a network interface device 1120. The implantable medical device interface can include a wired or wireless data connection with an implantable medical device. In an example, the implantable medical device (IMD) interface allows information stored in the IMD to be downloaded to the computer system 1100 for display or analysis. In an example, the information downloaded from the IMD can be displayed on the video display unit 1110. In another example, the information downloaded can be processed by the processor 1102 prior to display on the video display unit 1110. In an example, the IMD interface can also upload information, including programming parameters for an implantable CRM device, back into the IMD.

Machine-Readable Medium

The disk drive unit 1116 includes a machine-readable medium 1122 on which can be stored one or more sets of instructions and data structures (e.g., software) 1124 embodying or utilized by any one or more of the methodologies or functions described herein. The instructions 1124 can also reside, completely or at least partially, within the main memory 1104 or within the processor 1102 during execution thereof by the computer system 1100, the main memory 1104 and the processor 1102 also constituting machine-readable media.

While the machine-readable medium 1122 can be shown in an example embodiment to be a single medium, the term "machine-readable medium" can include a single medium or multiple media (e.g., a centralized or distributed database, or associated caches and servers) that store the one or more instructions or data structures. The term "machine-readable medium" can include any tangible medium that is capable of storing, encoding or carrying instructions for execution by the machine and that cause the machine to perform any one or more of the methodologies of the present application, or that is capable of storing, encoding or carrying data structures utilized by or associated with such instructions. The term "machine-readable medium" can include, but need not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks including internal hard disks and removable disks; magneto-optical disks; and CD-ROM and DVD-ROM disks.

Transmission Medium

The instructions 1124 can further be transmitted or received over a communications network 1126 using a transmission medium. The instructions 1124 can be transmitted using the network interface device 1120 and any one of a number of transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi and WiMax networks).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
   an implantable physiological data monitor, configured to monitor one or more physiological data parameters;
   a processor, coupled to the implantable physiological data monitor, the processor configured to,
      detect an episode beginning condition using a first physiological data parameter monitored by the implantable physiological data monitor, wherein the episode beginning condition is indicative of beginning of a present pathological episode; and
      detect an episode ending condition monitored by the implantable physiological data monitor, wherein the episode ending condition is indicative of the ending of the present pathological episode;
   a rolling memory buffer configured to continually store a fixed segment of a second physiological data parameter monitored by the implantable physiological data monitor;
   a static memory buffer configured to store a time segment of a third physiological data parameter monitored by the implantable physiological data monitor based on a triggering event associated with the detecting of the episode ending condition; and
   a memory configured to store data retained in the static memory buffer and associate the data retained in the static memory with the data retained in the rolling memory buffer for later use by the processor or for output to an external device.

2. The system of claim 1, wherein the processor is configured to detect the episode ending condition at least in part by determining that an implantable medical device has delivered a therapy.

3. The system of claim 1, wherein the therapy includes delivery of electrostimulation.

4. The system of claim 1, wherein the triggering event includes a specified delay after a time the episode ending condition is detected.

5. The system of claim 1, wherein detecting the episode ending condition includes using a fourth physiological data parameter monitored by the implantable physiological data monitor.

6. The system of claim 5, wherein the episode ending condition is detected when one or more of the first, second, third, and fourth monitored physiological parameters meet a specified test.

7. The system of claim 5, wherein the first physiological data parameter and the fourth physiological data parameter represent same physiological characteristics, the same physiological characteristics including the same at least one of heart rate, electrogram morphology, blood pressure, blood gas, blood chemistry, respiration rate, atrial versus ventricular heart rate, or heart rate stability.

8. The system of claim 1, wherein at least two of the first, second, and third physiological data parameters represent same physiological characteristics.

9. The system of claim 1, wherein at least two of the first, second, and third physiological data parameters represent different physiological characteristics.

10. The system of claim 1, wherein the implantable physiological data monitor includes one or more of: an electrocardiogram sensor, a heart rate sensor, a heart sounds sensor, a pressure sensor, a blood gas sensor, an electroneurogram sensor, a posture sensor, a respiratory sensor, or a chemical sensor.

11. A method, comprising:
monitoring first physiological data using an implantable physiological monitor;
using the first physiological data, detecting an episode beginning condition indicative of a beginning of a present pathological episode;
responding to detecting the episode beginning condition by collecting second physiological data associated with the detecting the episode beginning condition;
detecting an episode ending condition indicative of the ending of the present pathological episode;
responding to detecting the episode ending condition by collecting third physiological data associated with the detecting of the episode ending condition, wherein collecting the third physiological data is triggered after a specified delay beyond a time the episode ending condition.

12. The method of claim 11, wherein detecting the episode ending condition includes detecting the episode ending when an implantable cardiac rhythm management device has delivered a therapy.

13. The method of claim 12, wherein the therapy includes delivery of electrostimulation.

14. The method of claim 11, comprising monitoring fourth physiological data using the implantable physiological monitor.

15. The method of claim 14, wherein the episode ending condition is detected when the monitored fourth physiological data meets a test.

16. The method of claim 15, wherein the episode ending condition is detected when one or more of the first, second, third, and fourth monitored physiological data meet a test.

17. The method of claim 14, wherein at least the first and the fourth physiological data represent same physiological characteristics, the same physiological characteristics including the same at least one of heart rate, electrogram morphology, blood pressure, blood gas, blood chemistry, respiration rate, atrial versus ventricular heart rate, or heart rate stability.

18. The method of claim 11, wherein at least two of the first, second, and third physiological data represent the same physiological characteristic.

19. The method of claim 11, wherein at least two of the first, second, and third physiological data represent a different physiological characteristic.

* * * * *